(12) United States Patent
Zhang

(10) Patent No.: US 7,556,737 B2
(45) Date of Patent: Jul. 7, 2009

(54) ANAEROBIC PHASED SOLIDS DIGESTER FOR BIOGAS PRODUCTION FROM ORGANIC SOLID WASTES

(75) Inventor: Ruihong Zhang, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 131 days.

(21) Appl. No.: 11/641,348

(22) Filed: Dec. 18, 2006

(65) Prior Publication Data
US 2007/0158264 A1    Jul. 12, 2007

Related U.S. Application Data

(60) Provisional application No. 60/821,064, filed on Aug. 1, 2006, provisional application No. 60/751,027, filed on Dec. 16, 2005.

(51) Int. Cl.
*C02F 3/28* (2006.01)
*C02F 11/04* (2006.01)
(52) U.S. Cl. .................. 210/603; 210/613; 210/631; 210/202; 210/259

(58) Field of Classification Search .................. 210/603, 210/612, 613, 615–617, 631, 201, 202, 252, 210/259
See application file for complete search history.

(56) References Cited

U.S. PATENT DOCUMENTS

| 4,022,665 | A | * | 5/1977 | Ghosh et al. | 435/167 |
| 5,525,229 | A | * | 6/1996 | Shih | 210/603 |
| 5,529,692 | A | * | 6/1996 | Kubler | 210/603 |
| 5,630,942 | A | * | 5/1997 | Steiner | 210/603 |
| 5,670,047 | A | * | 9/1997 | Burke | 210/603 |
| 2003/0094410 | A1 | * | 5/2003 | Fassbender | 210/603 |

* cited by examiner

*Primary Examiner*—Fred Prince
(74) *Attorney, Agent, or Firm*—Morgan, Lewis & Bockius LLP; Jeffry S. Mann; Todd W. Esker

(57) ABSTRACT

The present invention provides methods for the generation of methane by a two phase anaerobic phase system (APS) digestion of organic substrates. Also provided is a device for practicing the methods of the invention. The APS-digester system is a space-efficient, high-rate solids digestion system. The APS-digester system consists of one or more hydrolysis reactors, a buffer tank and one biogasification reactor.

23 Claims, 11 Drawing Sheets

APS-DIGESTER SYSTEM FOR WASTEWATER DIGESTION

ANAEROBIC PHASED SOLIDS DIGESTER FOR BIOGAS PRODUCTION FROM ORGANIC SOLID WASTES

CROSS-REFERENCE TO RELATED APPLICATIONS

This application claims priority to U.S. Provisional Application No. 60/821,064 filed Aug. 1, 2006 and to U.S. Provisional Application No. 60/751,027, filed Dec. 16, 2005, the disclosures of which are incorporated herein by reference for all purposes.

BACKGROUND OF THE INVENTION

Anaerobic digestion has been known to stabilize sludge and other predominantly organic materials, and usable product gas, of varying composition, has been obtained from such anaerobic digestion processes. The organic feed mixture which provides the substrate for anaerobic biodegradation can comprise a wide variety of organic carbon sources, ranging from raw sewage sludge to municipal refuse, or biomass material such as plants and crop wastes. The process of anaerobic digestion degrades any of these organic carbonaceous materials, under appropriate operating conditions, to product gas which contains hydrogen and methane gases.

Anaerobic digestion uses a consortium of natural bacteria to degrade and then convert an organic substrate into a mixture of methane and carbon dioxide. The existing anaerobic digestion systems for organic substrate digestion can be separated into two major types, one phase systems and two phase systems. Existing one phase systems include the batch digester, completely mixed digester and the plug flow digester. These one phase systems, in which the organic substrate and the microorganisms are housed together are easy to operate and of low cost. Completely mixed digesters and plug flow digesters require continuous handling of feedstock and do not operate in batch mode. Further, the biogas produced in one phase systems consists primarily of carbon dioxide in the early stages of digestion. The high carbon dioxide content of the biogas is attributable to the slow growth of the methanogenic microorganisms and their inhibition by high concentrations of volatile fatty acids (VFAs). In order to reduce the inhibition of the microorganisms by the VFAs, the two phase digester has been introduced.

Separated two phase anaerobic digestion systems have been found to enhance the conversion efficiency, such as described in Pohland and Ghosh, Biotechnol. and Bio-eng. Symp. No. 2, 85-106 (1971), John Wiley and Sons, Inc. and by the same authors in Environmental Letters, 1: 255-266 (1971). A typical two phase anaerobic digester system comprises a hydrolytic and a biogasification reactor. The acid phase digester is usually designed as a solid-bed batch reactor where solid waste is housed and leached soluble compounds are collected. In the acid first phase, the microbial population and operating conditions are selected to promote the conversion of organic matter to soluble compounds of lower molecular weight, primarily VFAs. The liquid and solid effluent from the acid phase is conveyed to a biogasification second phase, where methanogenic organisms convert the VFAs to product gas that is composed primarily of methane and carbon dioxide. Product gas is removed from the biogasification reactor and processed, or scrubbed, to separate the methane component that is drawn off as pipeline gas.

Anaerobic digestion of solid waste, particularly agricultural residues and municipal organic solid wastes, is a promising technique for both generating energy and reducing the volume of waste which must be disposed of. The energy generated can be significant. For example, the energy content of a pound of rice straw is about 6,500 Btu (British Thermal Units), and the energy stored in the straw by growing crop each year in the Sacramento Valley is $1.95 \times 10^{12}$ Btu. One ton of food leftovers collected from restaurants could be used to produce $2.2$-$2.7 \times 10^6$ Btu biogas energy (Zhang et al., 2007), thus, it is realistic to consider agricultural residues and municipal organic wastes as a renewable resource for energy generation.

Anaerobic digestion is an enhanced biodegradation process that offers a promising alternative approach for helping solve problems caused by agricultural waste such as the imminent rice straw disposal problems in concentrated rice production regions such as California. It also offers a solution in reducing the greenhouse gas emissions from landfills where most of municipal organic wastes are disposed of. Anaerobic digestion uses a consortium of microorganisms to degrade and then convert a large portion of organic waste into biogas, which is a mixture of hydrogen, methane and carbon dioxide. If captured, biogas can be utilized as a clean fuel for heat and power generation or transportation.

However, the previously developed two phase anaerobic systems are not efficient systems. First, hydrogen produced by certain microorganism during the breakdown of organic matter is consumed by other microorganisms in the system, with the result that only methane is produced. It would more efficient if the microorganisms in the hydrolysis reactors are selected and environmental conditions are controlled to allow production and release of hydrogen in the first phase prior to methane production in the second phase. Second, the VFAs in the various hydrolysis reactors are not equilibrated when they enter in the biogasification reactor. Therefore, the methane-producing bacteria in the biogasification reactor do not react efficiently with the VFAs, resulting in inefficient gas production. Third, in the previously developed systems, a perforated plate is installed inside the hydrolysis reactor to separate liquid from solids and the outlet of the hydrolysis reactor is located at the bottom of the reactor to allow the decanting of liquid from the reactor. Such a design allows only a portion of the hydrolysis reactor to be utilized for the reaction, resulting in lower efficiency. Quite surprisingly, the present invention provides methods and devices which solve these problems.

SUMMARY OF THE INVENTION

The present invention provides many advantages. First, APS digester converts organic waste into hydrogen, methane and carbon dioxide gases which can be utilized as a clean fuel for heat and power generation or transportation. Second, the system is attractive commercially because it allows higher energy conversion efficiencies and less air emissions from engines if hydrogen, methane and carbon dioxide gases are used together as fuel. Third, the system uses a buffer tank which equilibrates physical and chemical properties of the VFA's (i.e., pH, temperature, conductivity, nutrients, biochemical oxygen demand, etc.) collected from different hydrolysis reactors and provide a means to control the VFA loading rate into the biogasification reactor. This equilibration process provides higher and more stable gas yields because bacteria in the biogasification reactor react more efficiently on equilibrated VFA's. Fourth, the outlet of the hydrolysis reactor is located on the side of the hydrolysis reactor. Maximum use of the hydrolysis reactor volume leads to the highest conversion efficiency of organic substrates, resulting in maximum gas production and lower capital cost. Fifth, hydrogen gas is also produced in the hydrolysis reactor and the buffer tank. The batch degradation processes used in the APS digester system in the hydrolysis tank allows the production of hydrogen gas to be stable with a high rate. When hydrogen is coupled to other gases (i.e., methane), the APS digester system becomes a more efficient system.

The anaerobic phase solids ("APS") digester system is a new type of two phase system. The system employs at least one hydrolysis reactor, one buffer tank, and a biogasification reactor. In the APS digester system, organic compounds in the organic substrates are liquefied into VFA's in the hydrolysis reactor. The soluble VFA's produced in the hydrolysis reactor are transferred through a side outlet to a buffer tank wherein the soluble VFA's are equilibrated with respect to physical and chemical properties. The equilibrated VFA's are then transferred to the biogasification reactor at a controlled rate so that the optimum growth rate of methanogenic bacteria can be achieved.

In a first aspect, the present invention provides a method for producing hydrogen, methane carbon dioxide and combinations thereof by a two-phase anaerobic digestion of organic material. The method includes: (a) incubating a first hydrolysis mixture in a first hydrolysis phase vessel for a first period of incubation, the first hydrolysis mixture comprising the solid organic material and an aqueous liquid, under anaerobic conditions, the first hydrolysis phase vessel comprising therein a hydrolytic bacterial culture for which the solid organic material is a substrate; (b) after the first period of incubation, transferring a portion of the aqueous liquid of the first mixture residing in the first hydrolysis phase vessel to a buffer tank, forming a buffer tank mixture; (c) transferring a portion of the buffer tank mixture to a gasification reactor comprising a methanogenic bacterial culture therein for which the volatile fatty acid is a substrate, forming a biogasification mixture; (d) incubating the biogasification mixture for a second incubation period during which gas which is a member selected from methane, hydrogen and mixtures thereof is generated; and (e) transferring a portion of the biogasification mixture into the first hydrolysis phase vessel for a third incubation period.

In an exemplary embodiment, the method comprises incubating a first mixture having a solid organic component and an aqueous liquid component, under anaerobic conditions, in a hydrolysis reactor. Hydrogen and carbon dioxide gases are primarily produced at this step. Methane gas can also be produced at this step as well. After a first period of incubation, a portion of the liquid component of the first mixture in the hydrolysis reactor is transferred to a buffer tank in which the soluble volatile fatty acids (VFA's) are equilibrated with respect to their physical and chemical properties (i.e., pH, temperature, conductivity, nutrients, biochemical oxygen demand, etc.). Hydrogen and carbon dioxide gases are also be produced in the buffer tank. The equilibrated VFA's are transferred to a methane phase digester and a methanogenesis media (e.g., a bacterial culture) therein. In the methane phase digester, the equilibrated VFA's are combined with the methanogenesis means to form a resulting mixture. The resulting mixture is incubated for a second period of time, generating methane and carbon dioxide gases. The resulting mixture is intermittently agitated, then allowed to remain still for a third period of time. After a selected period of time, a portion of the resulting mixture of the methane phase digester is recirculated back to the hydrolysis phase digester.

In a second aspect, the present invention provides an APS digester system for hydrogen and methane production. The system comprises a hydrolysis reactor which comprises an inlet and a side outlet. The device further comprises a buffer tank which has an inlet for receiving soluble VFA's and an outlet for transferring equilibrated VFA's. The device further comprises a biogasification reactor which comprises an inlet and an outlet and, optionally, an agitating means.

The hydrolysis reactor, the buffer tank and the biogasification reactor are connected via a series of conduits through which liquid can be transferred. Thus, the device also comprises a first conduit connecting the hydrolysis reactor outlet to the buffer tank inlet, a second conduit connecting the buffer tank outlet with the biogasification reactor inlet and a third conduit connecting the biogasification reactor outlet with the hydrolysis reactor inlet.

Other features, objects and advantages of the present invention and its preferred embodiments will become apparent from the detailed description that follows.

DETAILED DESCRIPTION OF THE INVENTION

Abbreviations and Definitions

Figure 1:
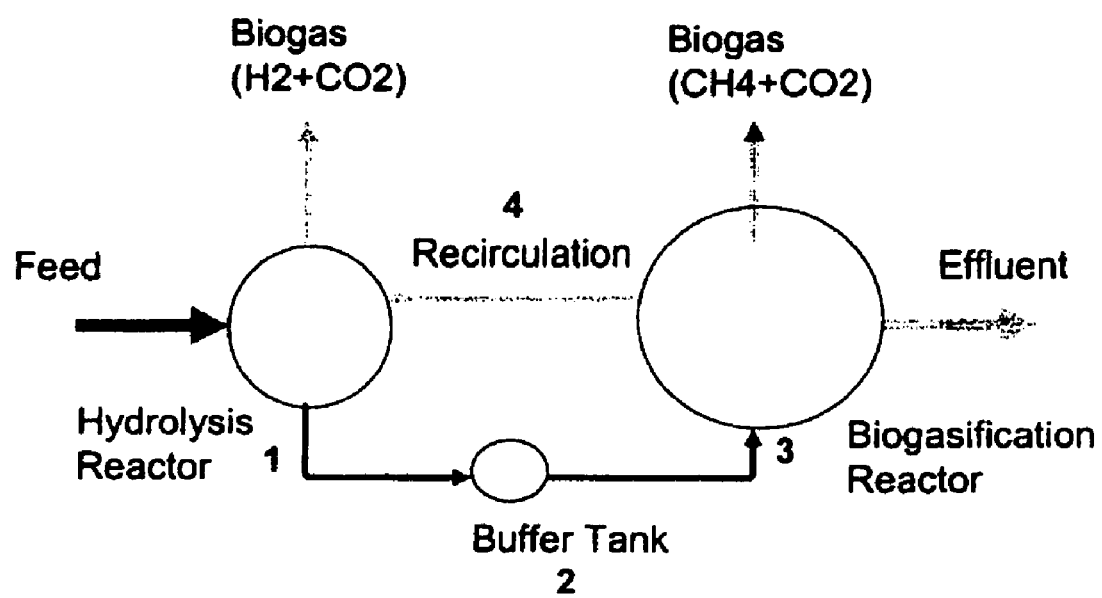
FIG. 1 is a diagram outlining an exemplary process of the APS-Digester System for wastewater digestion.

APS, anaerobic phased solids digester; VS, volatile solids; SRT, solid retention time; HRT, hydraulic retention time; VFA, volatile fatty acid.

As used herein, the term "organic substrate" refers to organic feedstock which can be used in the process and device of the invention to produce hydrogen and methane.

The terms "biogasification" and "methanogenesis" are used herein essentially interchangeably.

The present invention provides improved methods for the anaerobic digestion of waste to produce hydrogen and methane gases and devices with which to perform these methods.

The APS digester system is a new type of two phase anaerobic digestion system. The system employs at least one hydrolysis reactor, a buffer tank and a biogasification reactor. In the APS digester system, organic substrates are liquefied into VFAs in the hydrolysis reactor. The soluble VFAs are transferred to a buffer tank in which the physical and chemical properties of the VFAs are equilibrated. This allows controlled loading of VFAs into the biogasification reactor, resulting in the maintenance of a stable pH and temperature, therefore, stable and high production rate of methane gas. The equilibrated VFAs are then transferred to a biogasification reactor for production of gases. The remaining liquid in the biogasification reactor is then recirculated back to the hydrolysis reactor.

In a first aspect, the present invention provides a process for hydrogen and methane production by a two-phase anaerobic digestion of organic material. The process comprises incubating a mixture having a solid organic component and an aqueous liquid component, under anaerobic conditions and containing a hydrolysis means therein. Hydrogen and carbon dioxide gases are primarily produced in the hydrolysis reactor. Additionally, methane gas can also be produced in this process. After a first period of incubation, VFAs residing in the hydrolysis digester are transferred through an outlet located on the side of the hydrolysis reactor to a buffer tank in which physical properties of the VFAs are equilibrated. Hydrogen and carbon dioxide gases could also be produced in the buffer tank. After the VFAs are equilibrated, the equilibrated VFAs are transferred to a methane phase digester (biogasification reactor) and a methanogenesis means therein. In the methane phase digester, the equilibrated VFAs are combined with the methanogenesis means to form a resulting mixture. The resulting mixture is incubated for a second period of time, generating methane and carbon dioxide gases. The resulting mixture is optionally intermittently agitated, then allowed to remain still for a selected period of time. After the selected period of time, a portion of the resulting mixture residing in the methane phase digester is recirculated back to the hydrolysis reactor.

The process of the invention can be practiced with any carbonaceous organic substrate including, but not limited to, sewage sludge, forestry waste, food waste, agricultural waste, municipal waste, and the like.

Municipal waste primarily contains cellulosic products food wastes, grass clippings, tree trimmings, and paper products. It is known that such cellulosics can be digested as well as the minor amounts of waste protein, carbohydrates and fat present in municipal waste.

In a presently preferred embodiment, the organic substrate consists, at least in part, of an agricultural waste. Agricultural wastes include both plant and animal wastes. Many types of agricultural waste can be used in conjunction with the present invention. Useful agricultural wastes include, but are not limited to, foliage, straw, husks, fruit, manure and the like.

The hydrolysis phase, the buffer tank and the methanogenesis phase are operative over variable pH ranges that are related to the nature of the organic substrate and the amount of total solids in the organic substrate. In a preferred embodiment, the pH of the hydrolysis reactor is maintained from about 4.5 to about 7.0. In another preferred embodiment, the biogasification phase pH is maintained from about 6.5 to about 8.0.

The entire system is operated at a constant or variable temperature between about 10° C. to about 70° C., more preferably between about 35° C. to about 65° C., and most preferably between about 40° C. to about 60° C.

The buffer tank equilibrates physical and chemical properties of the VFAs before the VFAs enter into the biogasification reactor. Physical and chemical properties include, but are not limited to, temperature, pH, conductivity, nutrients, and biochemical oxygen demand. The VFAs which are equilibrated with respect to physical and chemical properties react more efficiently with bacteria in the biogasification reactor, resulting in higher gas production rate and yields.

Any art known hydrolysis or methanogenesis means can be used in the present invention. These include, but are not limited to acids, bases, enzymes and combinations of these substances. In a presently preferred embodiment, the hydrolysis and methanogenesis means are microorganisms.

In another embodiment, the concentration in the hydrogen gas collected from the hydrolysis(s) reactor is between about 10% to about 60%, more preferably between about 20% to about 50% and most preferably about 35%.

In another embodiment, the concentration of the methane gas collected from the biogasification reactor is between about 40% to about 80%, more preferably between about 50% to about 70% and most preferably about 60%.

In one embodiment, the recirculation of liquid from the biogasification reactor to the hydrolysis reactor can be a continuous process (i.e., 24 hours a day). In another embodiment, the recirculation of liquid from the biogasification reactor to the hydrolysis reactor can be an intermittent process. In a preferred embodiment, the recirculation process can occur for at least one second. In a preferred embodiment, the recirculation process can occur for at least one minute. In another preferred embodiment, the recirculation process can occur for at least one hour. In another embodiment, the recirculation process can occur for at least eight hours. In another embodiment, the recirculation process can occur for at least sixteen hours.

Any active hydrolytic or methane producing mesophilic or thermophilic anaerobic digestion system can be used in the present invention. In one embodiment, hydrogen-producing anaerobic systems utilize microorganisms from the *Clostridium* species. In an exemplary embodiment, the *Clostridium* species includes, but is not limited to, *C. thermolacticum*, *C. thermohydrosulfuricum*, *C. thermosuccinogene*, *C. butyricum*, *C. pasteurianum*, and *C. beijirincki*. In another embodiment, hydrogen-producing anaerobic systems utilize microorganisms from the *Lactobacillus* species. In an exemplary embodiment, the *Lactobacillus* species includes, but is not limited to, a *Lactobacillus paracasei*. In another embodiment, hydrogen-producing anaerobic systems utilize microorganisms from the *Eubacteria* species. In an exemplary embodiment, the *Eubacteria* species includes, but is not limited to, an *E. aerogenes*.

Currently preferred hydrolytic organisms include *Clostridium*, *Lactobacillus* and other Firmicutes and Proteobacteria.

Methane-producing anaerobic systems utilizing acid forming bacteria and methane-producing organisms, as are well known to be employed to produce methane from sewage sludge, can be employed in the practice of the present invention. A review of the microbiology of anaerobic digestion is set forth in Anaerobic Digestion, 1. The Microbiology of Anaerobic Digestion, D. F. Toerien and W. H. J. Hattingh, Water Research, Vol. 3, pages 385-416, Pergamon Press (1969). As set forth in that review, the principal suitable acid forming species include, species from genera including, but not limited to, *Aerobacter, Aeromonas, Alcaligenes, Bacillus, Bacteroides, Clostridium, Escherichia, Klebsiella, Leptospira, Micrococcus, Neisseria, Paracolobacterium, Proteus, Pseudomonas, Rhodopseudomonas, Sarcina, Serratia, Streptococcus* and *Streptomyces*. Also of use in the present invention are microorganisms which are selected from the group consisting of *Methanobacterium oinelianskii, Mb. formicium, Mb. sohngenii, Methanosarcina barkeri, Ms. methanica* and *Mc. mazei* and mixtures thereof.

Currently preferred methanogenic organisms include *Methanobacteriaceae, Methanosarcinaceae, Methanosaetaceae, Methanocorpusculaceae, Methanomicrobiaceae*, and other archae organisms.

Other useful microorganisms and mixtures of microorganisms will be apparent to those of skill in the art.

A wide variety of substrates are utilized by the methane producing bacteria, but each species is believed to be characteristically limited to the use of a few compounds. It is therefore believed that several species of methane producing bacteria are required for complete fermentation of the compounds present in certain organic substrates such as sewage. For example, the complete fermentation of valeric acid requires as many as three species of methane producing bacteria. Valeric acid is oxidized by *Mb. Suboxydans* to acetic and propionic acids, which are not attacked further by this organism. A second species, such as *Mb. Propionicum*, can convert the propionic acid to acetic acid, carbon dioxide and methane. A third species, such as *Methanosarcina methanica*, is required to ferment acetic acid.

An operative mixed culture is capable of sustaining itself indefinitely as long as a fresh supply of organic materials is added because the major products of the fermentation are gases, which escape from the medium leaving little, if any, toxic growth inhibiting products. Mixed cultures generally provide the most complete fermentation action. Nutritional balance and pH adjustments can be made as is known in the art to favor hydrolytic activity.

Mechanical degradation or chemical treatment of the organic substrate may be required either to achieve a particle size appropriate for use in anaerobic digestion according to the invention or to render the carbonaceous components of the organic substrate more accessible to the digestion media. Suitable methods of mechanical degradation are known in the art. Various pretreatment of the organic substrate can advantageously be used with the present invention, such as acid or alkaline hydrolysis.

The method also contemplates the selective use of predigestion hydrolysis of the organic substrate before introduction into the hydrolysis reactor, as well as post biogasification hydrolysis of waste removed from the biogasification phase. The hydrolysis can be conducted as mild acid or mild alkaline hydrolysis, optionally followed by neutralization of the added acid or alkali. The hydrolysis can also be performed using biological means.

In an exemplary embodiment, the organic substrate is agricultural waste, e.g., rice straw. Previous research has demonstrated the feasibility of anaerobically digesting a mixture of straw (rice straw and wheat straw) and other agricultural and food wastes, such as animal manure, green leaves and molasses, using conventional digestion reactors fed in batches or semicontinuously (Hills, D. J. and D. W. Roberts, Agricultural Wastes 3:179-189 (1981); Dar, G. H. and S. M. Tandon, Biological Wastes 21:75-83 (1987); Adbullah et al., Journal of Agricultural Sciences 119:255-263 (1992); Somayaji, D. and S. Khanna, World Journal of Microbiology & Biotechnology 10:521-523 (1994)). The research of Hills and Roberts (1981) showed that adding either chopped rice straw or chopped wheat straw to dairy manure enhanced the anaerobic digestion process and increased the methane production.

Rice straw is a ligno-cellulosic material mainly composed of cellulose (37.4%), hemicellulose (44.9%), lignin (4.9%), and silicon ash (13.1%) (Hills, D. J. and D. W. Roberts, Agricultural Wastes 3:179-189 (1981)). The straw contains about 0.4% nitrogen and has a carbon to nitrogen ratio (C/N) of around 75. The proper range of C/N ratio for anaerobic digestion is 25-35 (Hills, D. J. and D. W. Roberts, Agricultural Wastes 3:179-189 (1981)). Therefore, nitrogen needs to be supplemented in order to effect the anaerobic digestion of rice straw. Nitrogen can be added in inorganic forms, such as ammonia, or in organic forms such as organic nitrogen contained in urea, animal manure or food wastes. But once nitrogen is released from the organic matter, it will become ammonia ($NH_4+$) which is water soluble. Recycling of nitrogen in the digested liquid will reduce the amount of nitrogen needed for continuous operation of anaerobic digesters. Animal manures and food wastes are good nutrient sources if they are readily available in the areas close to rice straw production. Nitrogen fertilizer, such as ammonia or urea, is another source of nitrogen that can be easily added to the straw and may be more suitable for the areas where handling other types of wastes is not feasible.

Thus, in a preferred embodiment, the organic substrate is supplemented with a nitrogen source. In a further preferred embodiment, the nitrogen source is a member selected from the group consisting of urea, animal manure, food waste, inorganic nitrogen fertilizers and combinations thereof.

Thus, in a preferred embodiment, the organic feedstock, particularly agricultural waste (e.g., rice straw) is pretreated by a chemical treatment method selected from the group consisting of bicarbonate treatment, alkaline peroxide treatment, radiation treatment, ammonia treatment and combinations thereof.

The ammonia treatment shows several advantages over the other treatment, such as the presence of hydroxyl ions as a delignification factor, a source of nitrogen for biodegradation, and no separate waste water streams generated from the pretreatment process. Thus, in a presently preferred embodiment, the feedstock is treated with aqueous ammonia. In a further preferred embodiment, the ammonia is present in an amount of from about 0.5% to about 10%, more preferably from about 1% to about 5% relative to the total weight of solids derived from feedstock.

Mechanical size reduction of organic feedstock also aids with the biodegradation by increasing surface area and rupturing cell walls and making the biodegradable components more accessible to microorganisms. Thus in a preferred embodiment, the feedstock is pretreated by a physical process selected from the group consisting of grinding, cutting, heating and combinations thereof. In another preferred embodiment, the organic feedstock is pretreated using a method comprising grinding the feedstock to a size from about 5 millimeters to about 50 millimeters. In a further preferred embodiment, the feedstock is heated to a temperature of from about 50° C. to about 120° C., more preferably from about 60° C. to about 90° C.

In another aspect, the present invention provides an anaerobic phased solids digester system for hydrogen and methane production. The system comprises at least one hydrolysis reactor, a buffer tank and a biogasification reactor. The hydrolysis reactor has at least one liquid inlet, at least one side liquid outlet and at least one outlet for gas produced in the hydrolysis vessel (e.g., methane, carbon dioxide, hydrogen and combinations thereof). The buffer tank also has at least one liquid inlet, at least one liquid outlet and at least one outlet for gas produced by the hydrolysis feed mixture in the buffer tank (e.g., methane, carbon dioxide, hydrogen and combinations thereof). Similarly, the biogasification reactor has at least one liquid inlet, at least one liquid outlet and at least one outlet for gas produced by the hydrolysis feed mixture in the buffer tank (e.g., methane, carbon dioxide, hydrogen and combinations thereof).

The present system utilizes transfer (e.g., decanting) of the liquid from a hydrolysis tank, which contains VFA's, through one or more openings on the side wall of the hydrolysis tank using a solid-liquid separation device (e.g., screen, mesh, grate, filter, etc.). In a preferred embodiment, the separation device results in transfer of a substantially liquid (e.g., essentially devoid of solids) hydrolysis feed solution into the buffer tank. It is generally preferred that the content of the hydrolysis feed solution on a weight/weight basis is at least about 80% liquid, preferably at least about 90%, more preferably at least about 95%, and more preferably includes less than about 5% solids.

The side position of the outlet results in a greater working volume capacity in the hydrolysis reactor. Greater working volume of the hydrolysis reactor leads to less capital cost and high process efficiency.

In contrast to the present system, the device disclosed in U.S. Pat. No. 6,342,378, includes a hydrolysis tank divided into two compartments. A first compartment at the lower end of the tank contains the aqueous solution with the hydrolysis products with a minimum amount of the solid feedstock; a second compartment at the upper end of the tank includes a slurry of the feedstock and an aqueous solution. The hydrolysis feed solution is collected in the first compartment and removed from the bottom of the tank. The two-compartment design reduces the volume in the tank available for feedstock and its hydrolysis.

In a presently preferred embodiment, the hydrolysis vessel contains a slurry of organic feedstock and an aqueous liquid to at least 50%, preferably at least 60%, more preferably at least 70%, even more preferably at least 80% and even more preferably at least 90%, 95% or essentially 100% of the internal capacity of the hydrolysis vessel.

In a preferred embodiment, the hydrolysis feed solution is transferred from a hydrolysis vessel into a buffer tank where it is equilibrated with another hydrolysis feed solution from a different hydrolysis vessel. Equilibration of the hydrolysis feed solutions from two or more hydrolysis vessels minimizes sudden changes in VFA concentration, pH and liquid content occurring when the hydrolysis feed solution is transferred directly from the hydrolysis vessel into the biogasification reactor. The equilibration of the hydrolysis feed solutions stabilizes the biogasification reactor and enhances the amount of gas formed by the reactor.

The hydrolysis reactor and the buffer tank are connected via series of conduits through which liquid from one reactor can be transferred to buffer tank. Thus, the device also comprises a first conduit connecting the hydrolysis reactor outlet to the buffer tank inlet, a second conduit connecting the buffer tank outlet to the biogasification reactor inlet and a third conduit connecting the biogasification reactor outlet with the hydrolysis reactor inlet.

The volume capacity of the hydrolysis reactor is variable depending on the need being answered by the device of the invention. In one embodiment, the hydrolysis reactor can hold at least 1, 10, 100, 1,000, 10,000, 100,000 or 300,000 gallons of liquid.

Similarly, the volume capacity of the buffer tank is variable. In one embodiment, the buffer tank can hold at least 1, 10, 100, 1,000, 10,000, 100,000 or 300,000 gallons of liquid.

Likewise, the volume capacity of the biogasification reactor is also quite enormous. In one embodiment, the biogasification reactor can hold at least 1, 10, 100, 1,000, 10,000, 100,000 or 300,000 gallons of liquid.

In a preferred embodiment, the system of the invention comprises two or more hydrolysis reactors. Any number of hydrolysis reactors can be used in conjunction with the present invention. In a preferred embodiment, the system utilizes from 1 to 15 hydrolysis reactors, more preferably from 2 to 14 hydrolysis reactors, even more preferably from 3 to 13 hydrolysis reactors, and still more preferably from 4 to 12 hydrolysis reactors. A particularly preferred embodiment includes at least 4 hydrolysis reactors, preferably at least 8 hydrolysis reactors and even more preferably at least 12 hydrolysis reactors.

The hydrolysis reactors and the buffer tank can be linked in fluid communication in any useful arrangement. Exemplary linking arrangements include parallel linking, series linking and combinations thereof. For example, the hydrolysis reactors can be linked in parallel with the buffer tank. Alternatively, the hydrolysis reactors can be linked in series with other hydrolysis reactors and this hydrolysis manifold can be linked to the buffer tank. In still another embodiment, more than one manifold of hydrolysis reactors in series or parallel can be linked in parallel or in series with the buffer tank.

Each of the hydrolysis reactors is preferably in line with the buffer tank (i.e., linked parallel with the buffer tank), feeding an aqueous solution of hydrolysis products (e.g., VFA's) into the buffer tank prior to their being transferred into the biogasification reactor. In a preferred embodiment, the hydrolysis feed solution from each hydrolysis tank is transferred directly into the buffer tank prior to being transferred into the biogasification reactor.

The contents of one or more of the hydrolysis vessel(s), the buffer tank or the bigasification reactor can be agitated either continuously or periodically during the hydrolysis/biogasification cycle. Any means known in the art for agitating a liquid or suspension can be used in the system of the invention. Exemplary means include, but are not limited to, overhead stirrers, gas or motor driven stirrers, magnetic stirrers, shakers, homogenizers, sonicators, gas bubbling tubes, ebulliators and the like. Other useful agitating means will be apparent to those of skill in the art.

The solids feedstock, e.g., crop residues, rice straw, green waste, municipal waste, etc., and a bacterial culture are contained in the hydrolysis reactor. Each hydrolysis reactor works with batches or semibatches while the biogasification reactor produces biogas continuously. In a preferred embodiment, the feedstock is fed into the hydrolysis reactor from the top of the reactor in batches or semibatches. Hydrogen and carbon dioxide gases are primarily produced in this process. Additionally, methane gas can also be produced in this process. After the feedstock is continuously hydrolyzed during each batch treatment, the soluble substances produced in the hydrolysis reactor are transferred to the buffer tank for equilibration. Hydrogen and carbon dioxide gases can also produced in the buffer tank. The equilibrated soluble substances are transferred intermittently to the biogasification reactor for continuous biogas production. The biogasification reactor contains microorganisms which produce methane and carbon dioxide gas. After completing a digestion cycle, the digested straw is removed from the hydrolysis reactor before a new batch of straw is added.

In a preferred embodiment, the reduction in total solids (TS) achieved by the process is at least about 50%, preferably at least about 60% and more preferably at least about 90%.

In another preferred embodiment, the reduction in volatile solids is at least about 60%, more preferably at least about 70% and even more preferably at least about 80%.

In an exemplary embodiment, the TS and VS reductions were, respectively, at least about 70% and at least about 80% for food waste, At least about 70% and at least about 80% for mixture of food and green wastes, and at least about 50% and at least about 70% for green waste.

In yet another preferred embodiment, the average biogas yield of the system and method of the invention is at least 300 mL/gVS, preferably at least 400 mL/gVS and still more preferably at least 500 mL/g/VS.

A preferred method and system of the invention provides methane yields of at least about 200 mL/gVS, preferably at least 300 mL/gVS and still more preferably at least 400 mL/g/VS.

An exemplary process of the hydrogen and methane gas production is described in FIG. 1.

The feed solution, containing organic substrates, is fed into the hydrolysis reactor 1. The hydrolysis reactor contains at least sufficient liquid to wet the organic substrates in the hydrolysis reactor and convert the organic substrates to VFAs. After a period of incubation in the hydrolysis reactor, hydrogen, methane and/or carbon dioxide gases are produced.

The VFA's are then transferred from the hydrolysis reactor into the buffer tank 2 via a first conduit. The hydrolysis feed solution from two or more hydrolysis vessels, containing VFA's, are equilibrated within the buffer tank respect to their physical properties (e.g., temperature, pH, VFA concentration, etc.). Hydrogen, methane and/or carbon dioxide may be generated in the buffer tank.

The equilibrated hydrolysis mixture is transferred to a biogasification reactor 3 via a conduit. After a period of incubation in the biogasification reactor, methane, hydrogen and/or carbon dioxide gases are produced. Additionally, effluent in the biogasification reactor is pumped away.

Following a period of incubation and digestion in the biogasification reactor, the resulting liquid in the biogasification reactor is optionally recirculated back into the hydrolysis reactor 4 via a third conduit.

Figure 2:
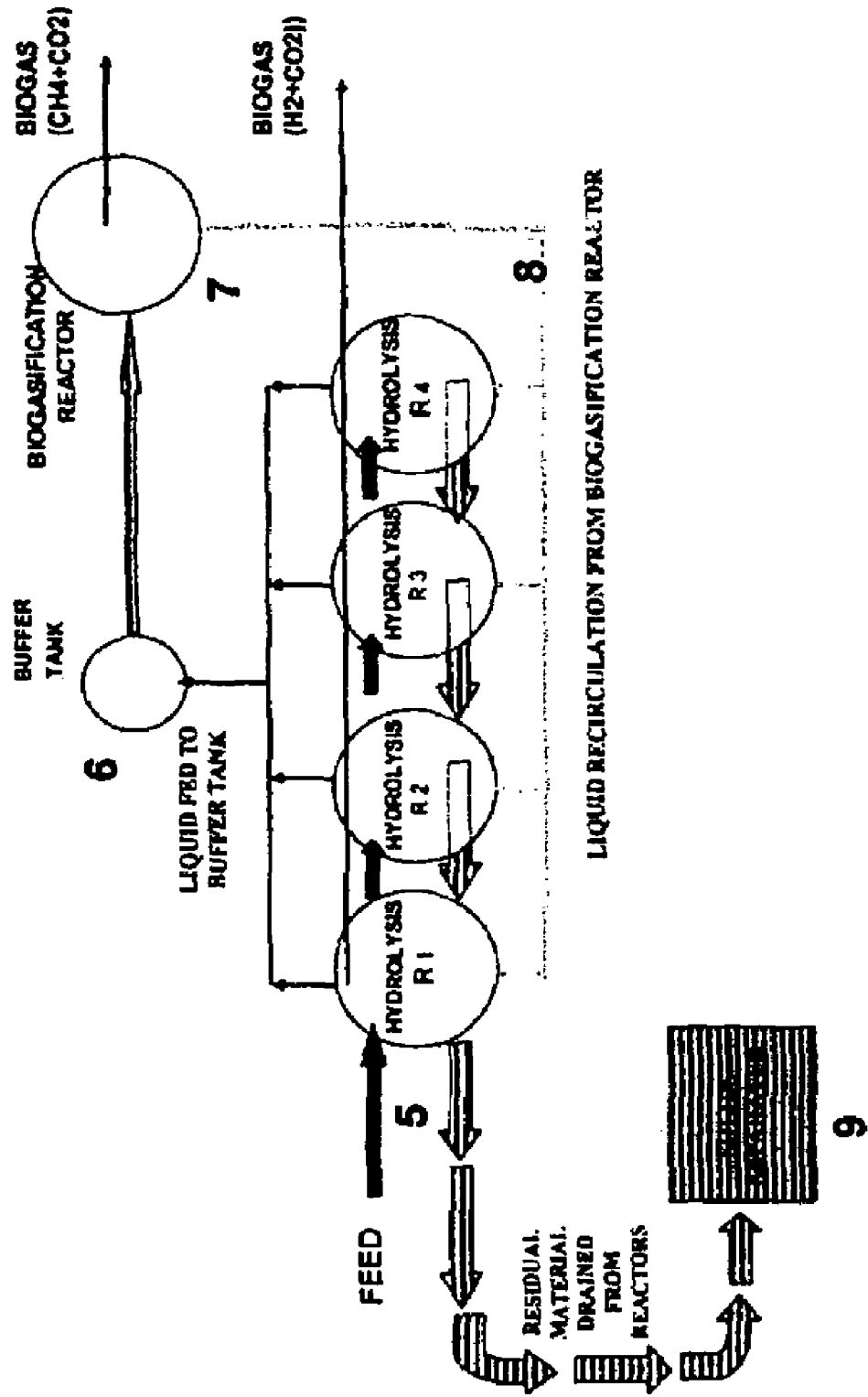
FIG. 2 is a diagram outlining an exemplary process of the APS-Digester System for solid waste digestion.

A detailed exemplary process for production of hydrogen and methane gas is described in FIG. 2.

The organic feedstock is fed into four hydrolysis reactors 5. The hydrolysis reactor contains at least sufficient liquid to wet the organic substrate in the hydrolysis reactor. After a period of incubation in a hydrolysis reactor, hydrogen and carbon dioxide gases are produced.

The liquid containing the hydrolyzed organic substrate is then transferred from the hydrolysis reactors into the buffer tank 6 via a first conduit. This transfer process can be assisted by means of a positive drive pump located inside the hydrolysis reactor, or a negative drive pump located inside the buffer tank. The hydrolysis solutions from the hydrolysis vessels are equilibrated with respect to their physical properties. Hydrogen, methane and/or carbon dioxide may be produced by the mixture in the buffer tank.

The equilibrated hydrolysis solution is transferred to biogasification reactor 7 via a conduit. After a period of incubation in the biogasification reactor, hydrogen, methane and/or carbon dioxide gases are produced.

Following a period of incubation and digestion in the biogasification reactor, the remaining liquid can be recirculated back into the four hydrolysis reactors 8 via a third conduit. This recirculation can be assisted by a pump with the caveat that the fluid flow is in the opposite direction, thus, the pumping direction must be similarly shifted.

Residual material in the four hydrolysis reactors can be transferred from the four hydrolysis reactors to a solids separator 9 wherein solids and liquids are separated from each other.

In certain preferred embodiments, the present invention provides:

A method for producing a gas which is a member selected from methane, hydrogen and combinations thereof using two-phase anaerobic digestion of solid organic material, the method comprising: (a) incubating a first hydrolysis mixture in a first hydrolysis phase vessel for a first period of incubation, the first hydrolysis mixture comprising the solid organic material and an aqueous liquid, under anaerobic conditions, the first hydrolysis phase vessel comprising therein a hydrolytic bacterial culture for which the solid organic material is a substrate; (b) after the first period of incubation, transferring a portion of the aqueous liquid of the first mixture residing in the first hydrolysis phase vessel to a buffer tank, forming a buffer tank mixture; (c) transferring a portion of the buffer tank mixture to a gasification reactor comprising a methanogenic bacterial culture therein for which the volatile fatty acid is a substrate, forming a biogasification mixture; (d) incubating the biogasification mixture for a second incubation period during which gas which is a member selected from methane, hydrogen and mixtures thereof is generated; and (e) transferring a portion of the biogasification mixture into the first hydrolysis phase vessel for a third incubation period.

A method according to the paragraph above, wherein step (a) further comprises: incubating a second hydrolysis mixture in a second hydrolysis phase vessel for a fourth period of incubation, the second hydrolysis mixture comprising the solid organic material and an aqueous liquid, under anaerobic conditions, the second hydrolysis phase vessel comprising therein a hydrolytic bacterial culture for which the solid organic material is a substrate.

A method according to any of the paragraphs above wherein step (b) further comprises: after the fourth period of incubation, transferring a portion of the aqueous liquid of the second hydrolysis mixture residing in the second hydrolysis phase vessel to the buffer tank mixture, thereby forming a buffer tank mixture which is an equilibrated liquid mixture comprising a volatile fatty acid component from each of the first and second hydrolysis phase vessel.

A method according to any of the paragraphs above, wherein step (e) further comprises: transferring a portion of the biogasification mixture into second first hydrolysis phase vessel for a fifth incubation period.

A method according to any of the paragraphs above, wherein the solid organic material is a member selected from the group consisting of sewage sludge, forestry waste, food waste, agricultural waste, green waste, municipal waste and combinations thereof.

A method according to any of the paragraphs above, further comprising collecting the gas generated in the first hydrolysis vessel and the biogasification reactor steps (c) through (e).

A method according to any of the paragraphs above, wherein the gas is generated in step (a).

A method according to any of the paragraphs above, further comprising collecting the gas generated in step (a).

A method according to any of the paragraphs above, wherein the first hydrolysis mixture has a pH of from about 4.5 to about 6.5.

A method according to any of the paragraphs above, wherein the second mixture has a pH of from about 6.5 to about 7.5.

A method according to any of the paragraphs above, wherein the bacterial culture in the first hydrolysis phase vessel is a member selected from the group consisting of *Clostridium, Lactobacillus, Eubacteria* species and combinations thereof.

A method according to any of the paragraphs above, wherein the bacterial culture in the biogasification reactor is a member selected from the group consisting of *Aerobacter, Aeromonas, Alcaligenes, Bacillus, Bacteroides, Clostridium, Eschericia, Klebsiella, Leptospira, Micrococcus, Neisseria, Paracolobacterium, Proteus, Pseudomonas, Rhodopseudomonas, Sarcina, Serratia, Streptococcus* and *Streptomyces, Methanobacterium omelianskii, Mb. formicium, Mb. sohngenii, Methanosarcina barkerii, Ms. methanica* and *Mc. mazei* and mixtures thereof.

A method according to any of the paragraphs above, wherein a member selected from the first hydrolysis vessel, the second hydrolysis vessel, the biogasification reactor and combinations thereof is agitated either continuously or intermittently.

A method according to any of the paragraphs above, wherein the first hydrolysis mixture is transferred from the first hydrolysis phase vessel to the buffer tank through a port on a vertical surface of the first hydrolysis phase vessel.

A method according to any of the paragraphs above, wherein the first hydrolysis phase vessel has an interior that is a single, undivided compartment.

A method according to any of the paragraphs above, wherein from about 80% to about 100% of the first hydrolysis vessel's interior volume contains the first hydrolysis mixture.

A method according to any of the paragraphs above, wherein step (a) further comprises incubating multiple hydrolysis mixtures in multiple hydrolysis phase vessels for multiple periods of incubation, the multiple hydrolysis mixtures comprising the solid organic material and an aqueous liquid, under anaerobic conditions, the multiple hydrolysis phase vessels comprising therein a hydrolytic bacterial culture for which the solid organic material is a substrate.

A method according to any of the paragraphs above, wherein the biogasification reactor comprises within it a surface area expanding material which is a medium appropriate for growth of the methanogenic bacterial culture.

An anaerobic phased solids digester system for production of gas from solid organic material, the system comprising: (a) a first hydrolysis phase vessel comprising therein a bacterial culture for which the solid organic material is a substrate, the hydrolysis vessel further comprising; (i) a vessel fluid inlet port communicating fluidically with a first conduit; and (ii) a vessel fluid outlet port located on a vertical surface of the hydrolysis phase vessel, the effluent port communicating fluidically with a second conduit; (c) a buffer tank comprising; (i) a buffer tank outlet port communicating fluidically with a third conduit; and (ii) a buffer tank inlet port communicating fluidically with the second conduit; (b) a biogasification reactor comprising therein a methanogenic bacterial culture, the biogasification reactor further comprising; (i) a reactor fluid inlet port communicating fluidically with the third conduit; and (ii) a reactor fluid outlet port communicating fluidically with the first conduit.

A digester system according to the paragraph above, further comprising between 1 and 15 additional hydrolysis phase vessels, each the additional vessel comprising: a bacterial culture therein for which the solid organic material is a substrate, each the hydrolysis vessel further comprising; (i) a vessel fluid inlet port communicating fluidically with a conduit communicating fluidically with a conduit communicating fluidically with the reactor fluid outlet port; and (ii) a vessel fluid outlet port located on a vertical surface of the hydrolysis phase vessel, the effluent port communicating fluidically with a conduit communicating fluidically with the buffer tank inlet port.

A digester system according to any of the paragraphs above, wherein the hydrolysis reactors and the buffer tank are linked in a manner selected from the group consisting of parallel linking, series linking and combinations thereof.

A digester system according to any of the paragraphs above, wherein the hydrolysis reactors are linked in parallel with the methanogenesis reactor.

A digester system according to any of the paragraphs above, wherein the vessel fluid outlet port further comprises a device for interfering with passage of solids into the second conduit.

A digester system according to any of the paragraphs above, wherein the device is a member selected from a grid, filter, grate, sieve, slats, strainer and combinations thereof.

A digester system according to any of the paragraphs above, further comprising a pump operably connected to a member selected from the first hydrolysis reactor, the buffer tank and the biogasification reactor.

A following examples are offered solely for the purposes of illustration, and are intended neither to limit nor to define the invention.

EXAMPLES

Example 1

1.1 Background

This study focused on the continuing development of Anaerobic Phased Solids Digester technology (APS-Digester), which was recently developed for digestion of solid waste as well as liquid waste (U.S. Pat. No. 6,342,378). Each hydrolysis reactor is operated as a batch reactor while the biogasification reactor is operated as a continuous reactor. The whole system was operated as a continuous system by staggering the feeding schedule of four batch hydrolysis reactors in sequential fashion. The feedstock material was retained in each hydrolysis reactor for a predetermined digestion period, and then the residual solids were removed from the reactor and processed through a solid-liquid separation device. The recovered liquid was put back into the hydrolysis reactor as the new feedstock is loaded. Depending on the moisture content of the feedstock, all or part of the recovered liquid was returned to the system.

This study was initiated to experimentally evaluate an APS-digester system consisting of four hydrolysis reactors coupled with one biogasification reactor. These experiments were designed to use food waste and green waste individually or as a mixture of both as feedstock in preparation for the development and optimization of a pilot-scale APS system being installed at the University of California at Davis (UC Davis).

The overall objective of this research was to determine the efficacy of using the APS-Digester system to treat food and green wastes. The specific objectives were to: (1) evaluate the performance of the APS-Digester system in terms of biogas and methane production rates and yields and solids reduction during the digestion of food waste, green waste and a mixture of the two at a thermophilic temperature of 55° C., and (2) determine the effects of different volume ratios of biogasification reactor to hydrolysis reactors on the performance of APS-Digester system.

1.2 Experimental Design

The first part of the experiment was dedicated to the start-up of the APS-Digester system with green waste and allowing the system to stabilize for about 72 days. After the system had stabilized, co-digestion experiments were conducted in which the performance of the APS-Digester system fed with a mixture of food and green wastes was tested at two BR/HR ratios. The BR/HR was calculated as the volume of biogasification reactor divided by the total volume of four hydrolysis reactors. The volume ratios of 1.0 and 0.5 were selected for evaluation; however the operating conditions gave slightly different liquid volumes in the biogasification reactor, resulting in these ratios to be 0.93 and 0.55, respectively. At the higher ratio, the volume of the biogasification reactor and the total volume of four hydrolysis reactors were 3.7 and 4 L, respectively, while at the lower ratio, they were 2.2 and 4 L, respectively. After finishing these two experimental runs (first and second), three more experimental runs were conducted: including digestion of food waste at a BR/HR of 0.55 (third run) and digestion of green waste at two BR/HR ratios, 0.55 and 0.25 (fourth and fifth runs). Table 1 shows the characteristics of the substrates used in each experiment. It should be mentioned that the BR/HR affect the hydraulic retention time (HRT) of the biogasification reactor when other system parameters (system cycle time, loading rates, feed volumes, etc.) were the same. Therefore, the calculated HRT of the biogasification reactor was 2, 1.2 and 0.54 days at a BR/HR ratio of 0.93, 0.55 and 0.25 respectively.

1.3 Feedstock Collection and Preparation

The green waste used in the start up period of the APS-Digester was collected from residential homes near Vacaville, Calif. After the collection, the green waste was passed through a screen with 10-cm openings to remove the impurities such as glass, wood and metals. The green waste used in the fourth and fifth experimental runs was lawn clippings collected on the campus of the University of California at Davis. Food waste was provided by a waste management company in Sacramento, Calif. It was collected from restaurants in the city of San Francisco and prepared by screening and grinding. After collection, the wastes were sampled and taken to the UC Davis Bioenvironmental Engineering Laboratory where they were analyzed and then stored at 4° C. until used for feeding the reactors. The characteristics of the green and food wastes used in the experiments are shown in Table 1. The total solids (TS), moisture content (MC) and volatile solids (VS) data are the average of at least three samples. Intention was made to use the same green and food wastes for all the digestion experiments but due to the spoilage of food waste in storage and availability of food waste, food waste collected at different times was used, which resulted in the slightly different characteristics of food waste as shown in Table 1. When the food and green wastes were digested together, enough feedstock for 24 days of digester operation was made from equal amounts of food and green wastes based on VS.

identical hydrolysis reactors (denoted as HR1, HR2, HR3 and HR3), a liquid collection tank and a biogasification reactor (BR).

The biogasification and hydrolysis reactors were constructed from acrylic tubing and capped with Poly Vinyl Chloride (PVC) fittings. Each hydrolysis reactor had a total volume of 2.4 L. Packed feed solids were kept submerged in the liquid at the 1-L level by a screen. Several ports were provided on the top and bottom of each reactor for biogas collection and liquid draining and return. The hydrolysis reactors received the liquid from the biogasification reactor on the top and drained from the bottom for liquid collection prior to its transfer to the biogasification reactor. Each hydrolysis reactor was operated as a batch reactor with liquid being transferred in and out during the 12-day solids digestion time. Loadings of the reactors with fresh feedstock were staggered so that one reactor was loaded every three days.

The liquid collection tank, with a total volume of 2 L, collected the liquid drained from the four hydrolysis reactors, and held it until the next feed cycle of biogasification reactor. The headspace of the collection tank was connected to the headspace of the biogasification reactor, but isolated from the headspaces of the hydrolysis reactors.

The biogasification reactor had a maximum total volume of 4.2 L. Different working volumes of biogasification were adjusted depending on different testing BR/HR ratios shown in Table 1. The reactor was operated as an Anaerobic Mixed Biofilm Reactor (AMBR). Approximately 600 mL ring-type polyethylene biomedia pellets were suspended in the liquid near the top to provide surface area for microorganisms to attach to. The biomedia pellets had dimensions of approximately 1 cm long by 1 cm in diameter and a density of 0.95 g/cm$^3$. The reactor was decanted at the middle depth of the liquid. The whole digester system was controlled using an automated timer/controller (Model XL, Chrontrol, San Diego, Calif.).

1.5. Analysis and Measurements

Samples were taken from the feedstocks (green and food waste) and digested solids from hydrolysis reactors and analyzed for TS and VS contents according to the standard methods (APHA, 1998). The seed sludge used for reactor start up was analyzed for mixed liquor volatile suspended solids (MLVSS), mixed liquor suspended solids (MLSS), TS, and VS according to standard methods (APHA, 1998). The characteristics of seed sludge are shown in Table 2. The nutrients content were measured by the DANR Analytical Laboratory

TABLE 1

Experimental design and substrate characteristics used

| Run no. | Substrates | BR/HR | TS (%, w.b.) | MC (%, w.b.) | VS (%, w.b.) | VS/TS (%) | C (g/kg) | N (g/kg) | C/N | $NH_4$—N (ppm) |
|---|---|---|---|---|---|---|---|---|---|---|
| Start up | Green waste | 0.93 | 21.6 | 78.4 | 19.0 | 87.7 | — | — | — | — |
| 1 | Food waste + green waste | 0.93 | 25.7 | 74.3 | 21.4 | 83.2 | — | — | — | — |
| 2 | Food waste + green waste | 0.55 | 34.0 | 66.0 | 29.9 | 88.0 | — | — | — | — |
| 3 | Food waste | 0.55 | 30.9 | 69.1 | 26.0 | 87.0 | 46.8 | 3.2 | 14.8 | 972.5 |
| 4 | Green waste | 0.55 | 27.4 | 72.6 | 21 | 78 | 41.8 | 3.1 | 13.3 | 117.5 |
| 5 | Green waste | 0.25 | 27.4 | 72.6 | 21 | 78 | 41.8 | 3.1 | 13.3 | 117.5 |

1.4 APS-Digester System Description

The APS-Digester system was operated at 55±2° C. The temperature was controlled by housing all the reactors in a heated chamber. The experimental set-up of the APS-Digester system is shown in FIG. 1 and FIG. 2 with the liquid and gas flow paths indicated. The system consisted of four (http://danranlab.ucanr.org as described by Zhang et al. (Bioresource Technology, 98(4):929-935 (2007)). Daily biogas production from each reactor was measured using a wet tip gas meters (http://wettipgasmeter.com/), which were held in a controlled environment at 35° C. The measured daily biogas volume was adjusted to the volume at standard temperature (0° C.) and pressure (1 atm). Collected biogas was analyzed periodically for methane and carbon dioxide contents using a gas chromatograph (GC) (Model HP5890A, Hewlett Packard, Avondale, Pa.) equipped with a thermal conductivity detector. The pH of liquid samples from the biogasification effluent and the liquid collection tank were measured prior to loading of each hydrolysis reactor using a pH meter (Accumet AR50, Fisher Scientific, Pittsburgh, Pa.). For the experiment conducted with food waste ($3^{rd}$ experimental run), the biogas was analyzed for $H_2$, $CH_4$ and $CO_2$. Each GC analysis was run in duplicates.

1.6 APS-Digester System Startup

The biogasification reactor was initially seeded with the sludge taken from a thermophilic anaerobic digester at East Bay Municipal Utility District's (EB MUD) wastewater treatment facility in Oakland, Calif. The characteristics of the thermophilic seed sludge used for biogasification reactor are shown in Table 2. After inoculating the biogasification reactor, the first hydrolysis reactor was loaded with 100 gVS of green waste while the other three were loaded with water. The green waste loading was determined by the maximum amount of green waste that could be manually packed into a hydrolysis reactor. The remaining three hydrolysis reactors were brought online over a period of nine days by loading one reactor every three days.

TABLE 2

Characteristics of the thermophilic seed sludge for biogasification reactor

| Parameter | Value |
|---|---|
| TS (g/L) | 20.27 |
| VS (g/L) | 11.67 |
| VS (% TS) | 57.6 |
| MLSS (g/L) | 16.73 |
| MLVSS (g/L) | 10.45 |

1.7 APS-Digester System Operation

Following the digester system startup with green waste, the feedstock was changed to a mixture of food and green wastes. The mixture was composed of 50% food waste and 50% green waste (based on VS contents). The other experiments were conducted sequentially. The data reported here are from a 12-day digestion period conducted after the digester system had stabilized under the reported operating conditions.

Each hydrolysis reactor was unloaded and reloaded every three days. Unloading was accomplished by draining all of the liquid from the reactor and entirely removing the reactor from the digester system. The drained liquid was saved for the reloading phase. Solids were then manually pressed through a screen with 841-μm openings to separate the liquid which was then added with the new feed. For each feeding day, the pressed solids were measured for total weight and three samples were taken and analyzed for TS and VS. After being cleaned, the hydrolysis reactor was reloaded with fresh feedstock that contained 100 g VS. The recovered liquid was put back into the reactor with any required make-up tap water to reach a total volume of 1 L. The reloaded reactor was then returned to the APS-Digester system.

1.8 Data Analysis

Daily biogas yields were calculated for each day in the digestion trial using biogas using OLR values and rate data. One way ANOVA analysis was performed to determine if there was any statistical difference between biogas and methane production at different BR/HR ratios using the twelve data points from each experiment. These tests were performed using Microsoft Excel's data analysis package at a significance level of $\alpha=0.05$. Because the system is operating under steady-state conditions each day was considered to be a repeat trial. The ANOVA analysis used each data point as a replication and compared daily production values from the first digestion experiment to those in the second experiment.

1.9 Results and Discussion 1.9a Anaerobic Digester System Startup

The performance of the APS-Digester system was characterized by two parameters: (a) ability to produce methane-rich biogas, which was quantified by daily biogas production volume and methane content of biogas, and (b) effective treatment of the solids waste, which was quantified by TS and VS reductions in the feedstock after digestion. System stability was determined by monitoring pH and daily biogas production of all reactors.

Figure 3:
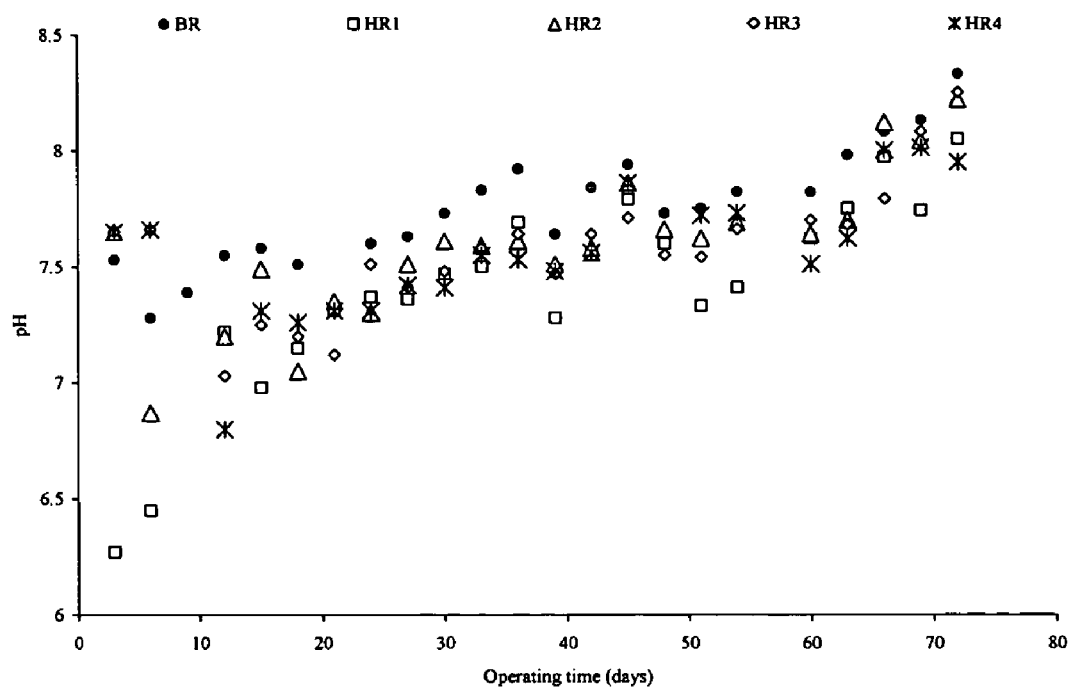
FIG. 3 is a plot of the pH of the five reactors in the APS-Digester System during the digestion of green waste in the APS-Digester system during the 72-day startup period.

The biogas production of the system during the first 60 days was variable and the biogas production data collected were not accurate due to the limitations of gas meters used (data not shown). The meters were replaced and the system stabilized before the data were collected for reporting. The pH in the system over the startup period was monitored to determine the stability of all reactors. Over a 72-day period, pH in all reactors increased to and stabilized near 8.25 (FIG. 3). The pH in each hydrolysis reactor cycled between a low value following each batch loading of the feedstock and higher values near the end of the batch digestion period. The low pH value in the hydrolysis reactors at the initial period was mainly due to the rapid production of organic acids from the degradation of readily hydrolyzed substances in the feedstock and then the pH increased as methanogenic bacteria established themselves within the reactor and began to consume the organic acids. Methane contents in the hydrolysis reactors were found to vary with respect to the digestion time. A low methane content of about 45% was found shortly after loading, whereas a high methane content of about 75% was reached towards the end of the digestion cycle. The methane content in the biogas produced in the biogasification reactor was consistently higher than the methane content in the biogas produced in the hydrolysis reactors at any point in their batch cycle (data not shown). This may indicate that the methanogenic and hydrolytic bacteria had been separated to some extent into their respective reactors. However, increasing methane content of the biogas produced in the hydrolysis reactors indicated that methanogenic bacteria were establishing themselves in the hydrolysis reactors over the 12-day batch digestion period.

1.9b Digestion of Green and Food Waste Mixture

Figure 4:
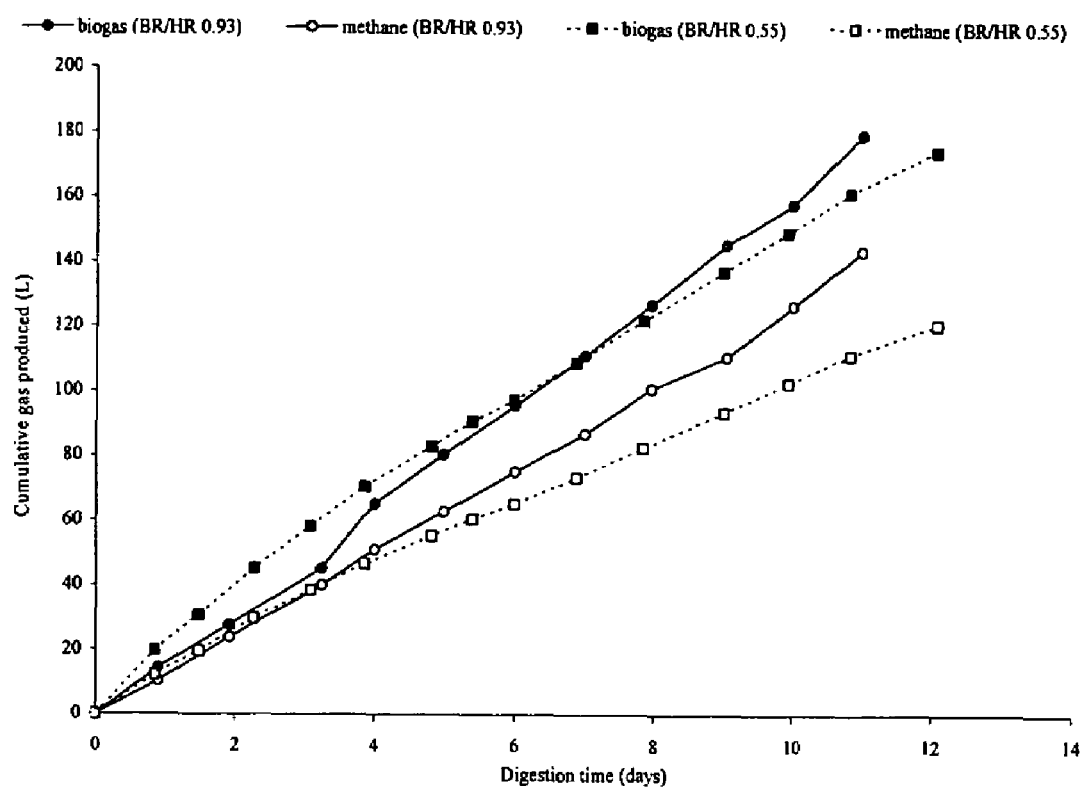
FIG. 4 is a plot of cumulative biogas and methane production in the APS-Digester system at volume ratios of biogasification reactor and hydrolysis reactor of 0.93 and 0.55.

The cumulative biogas and methane production at both studied BR/HR ratios during digestion of food and green waste mixture is shown in FIG. 4. The cumulative biogas and methane production was slightly higher at BR/HR of 0.93 than at BR/HR of 0.55.

The biogas and methane yields and TS and VS reduction are shown in Table 3. Biogas and methane values are the average of 12 measurements. TS and VS values are reported as the average of three measurements. The biogas yields from the digestion of the mixture were 537 and 461 mL/gVS, respectively for BR/HR of 0.93 and 0.55 and the methane yields were 430 and 319 mL/g VS, respectively. The solids reductions at BR/HR 0.55 were slightly higher than the reductions at BR/HR of 0.93. The increased VS and TS reductions suggest that the system would have produced greater amounts of biogas and methane, however the yields were slightly lower (Table 3).

TABLE 3

Experimental design and performance of the APS-Digester under different conditions

| Run No. | Substrates | BR/HR | Biogas yield (mL/gVS) | Methane yield (mL/gVS) | TS destruction (%) | VS destruction (%) |
|---|---|---|---|---|---|---|
| 1 | Food waste/green waste mixture | 0.93 | 537 | 430 | 72.4 | 74.8 |
| 2 | Food waste/green waste mixture | 0.55 | 461 | 319 | 77.3 | 81.8 |
| 3 | Food waste | 0.55 | 596 | 379 | 72.4 | 84.5 |
| 4 | Green waste | 0.55 | 438 | 252 | 57.8 | 78.0 |
| 5 | Green waste | 0.25 | 438 | 247 | 59.1 | 75.8 |

Statistical analysis of the data for digestion of food and green waste mixture showed no significant difference in biogas and methane yields between the two studied BR/HR ratios. This indicates that operating the APS-Digester system at the BR/HR of 0.55 would be both economically and functionally superior to the BR/HR of 0.93.

1.9c Digestion of Green Waste

Figure 5:
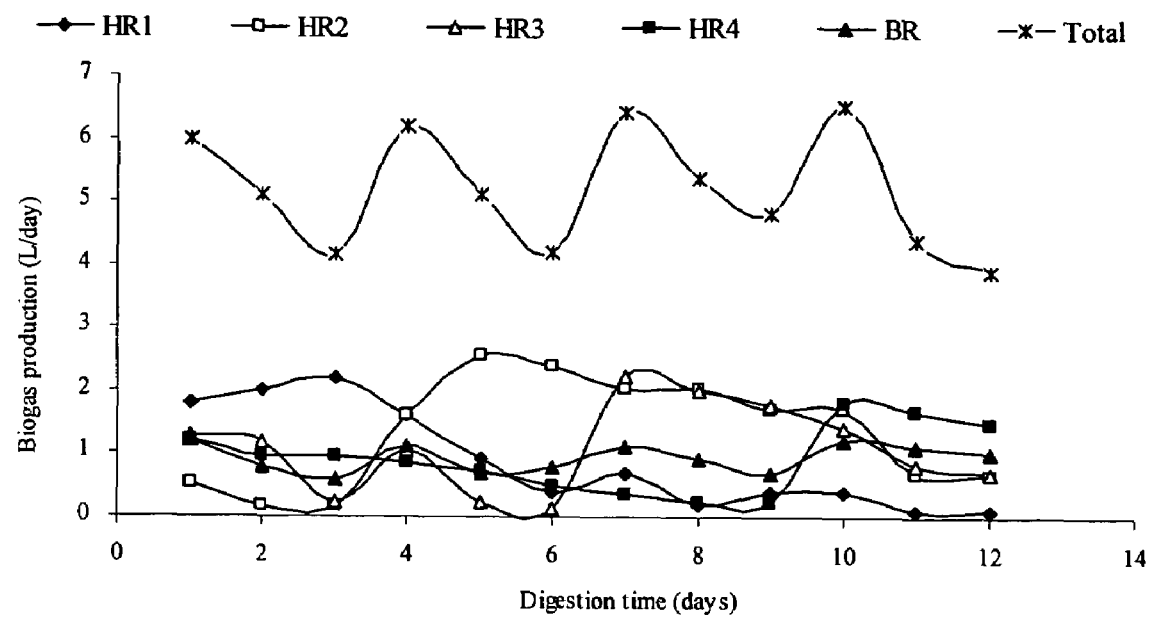
FIG. 5 is a plot of daily biogas production in five reactors of the APS-Digester system during digestion of green waste at a volume ratio of biogasification reactor and hydrolysis reactor of 0.55.
Figure 6:
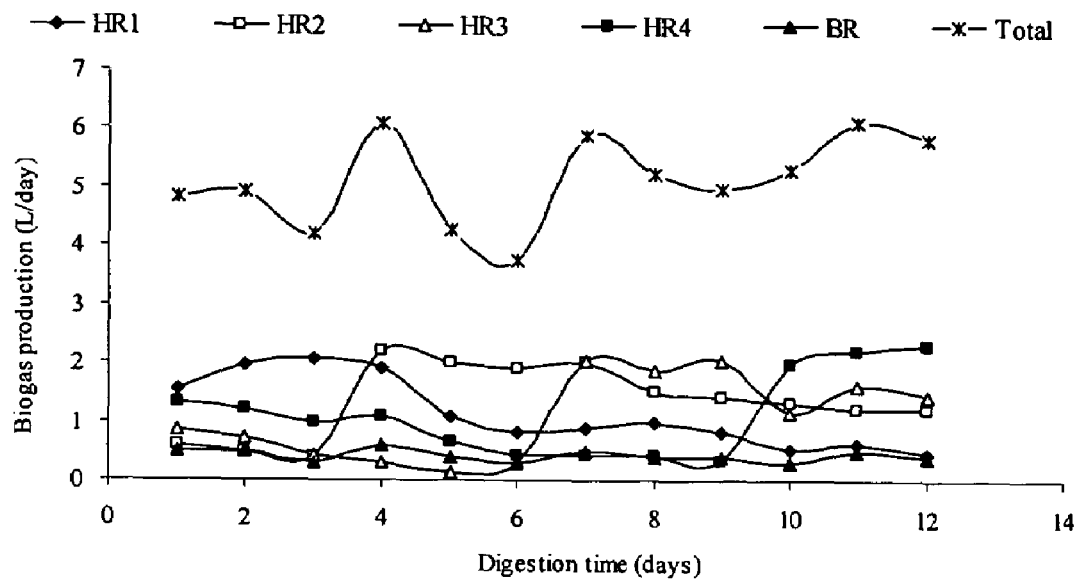
FIG. 6 is a plot of daily biogas production of five reactors of the APS-Digester system during digestion of green waste at a volume ratio of biogasification reactor and hydrolysis reactor of 0.25.

The daily biogas production rates from the five reactors in the APS-Digester system during the digestion of green waste at the BR/HR of 0.55 and 0.25 are shown in FIG. 5 and FIG. 6, respectively. Daily biogas production rates from each of the hydrolysis reactor were varied over the batch digestion time (12 days) with a higher rate shown after the loading of each hydrolysis reactor. On the other hand, the biogas production rate from the biogasification reactor was fairly constant over the digestion period. The total biogas production rate from the system varied between a maximum of 0.96 L/L/day and a minimum of 0.82 L/L/day for the BR/HR ratio of 0.55 and a maximum of 1.02 L/L/day and a minimum of 0.93 L/L/day for the BR/HR ratio of 0.25. An average biogas production rate of 0.86 and 0.98 L/L/day could be determined, respectively for the APS system having BR/HR ratio of 0.55 and 0.25. The biogas production from hydrolysis reactors in the APS—Digester system having BR/HR ratio of 0.55 is higher than that of 0.25. This may be attributed to the increase of the HRT from 2.4 to 14.3 days in the hydrolysis reactors.

Figure 7:
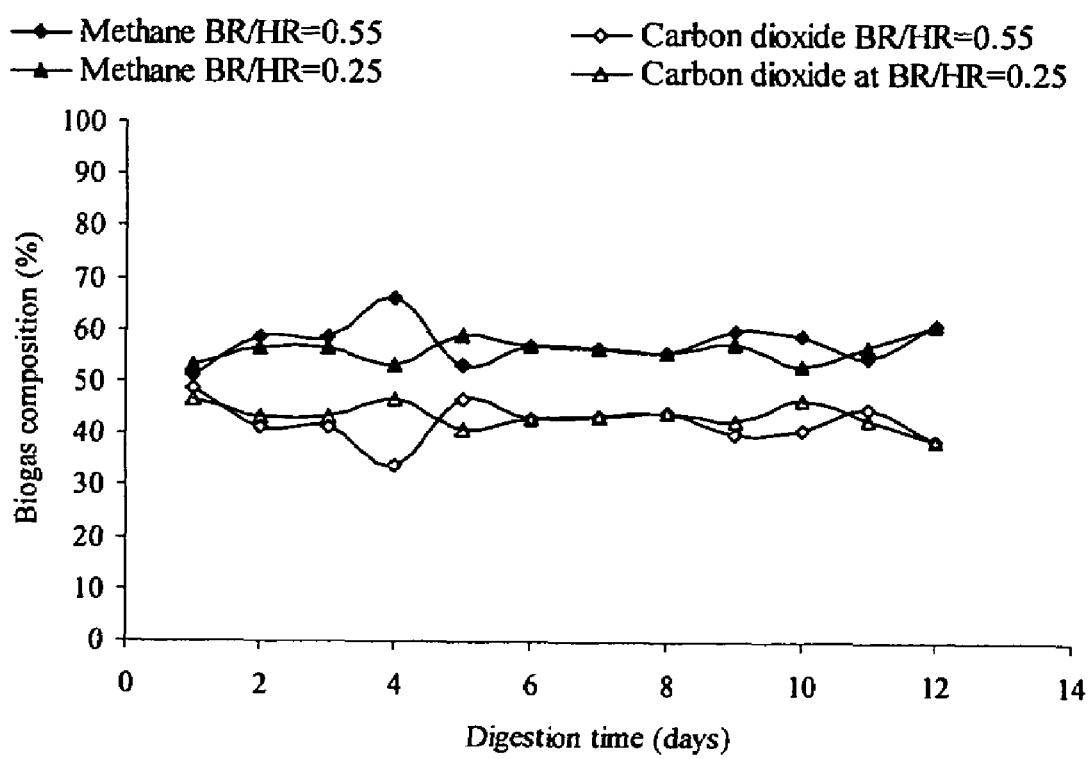
FIG. 7 is a plot of methane and carbon dioxide contents of biogas produced in the APS-digester system during digestion of green waste at two different volume ratios of biogasification reactor and hydrolysis reactor.

The average methane contents of the biogas produced from the APS-Digester systems are shown in FIG. 7. The methane production increased linearly over time. The average biogas and methane yields of green waste were determined to be, respectively, 438 and 252 mL/ for BR/HR of 0.55, and 318 and 175 mL/gVS for BR/HR of 0.25. The average TS and VS reductions in the feedstock after digestion were 57.8% and 78.0%, respectively, for the system of 0.55 BR/HR and 59.1% and 75.8%, respectively, for the system of 0.25 BR/HR. The average pH value of the liquid of the BR and the HR were 7.8 and 8.2, respectively with the BR/HR of 0.55 and 7.6 and 8.1 with the BR/HR of 0.25.

1.9d Digestion of Food Waste

Figure 9:
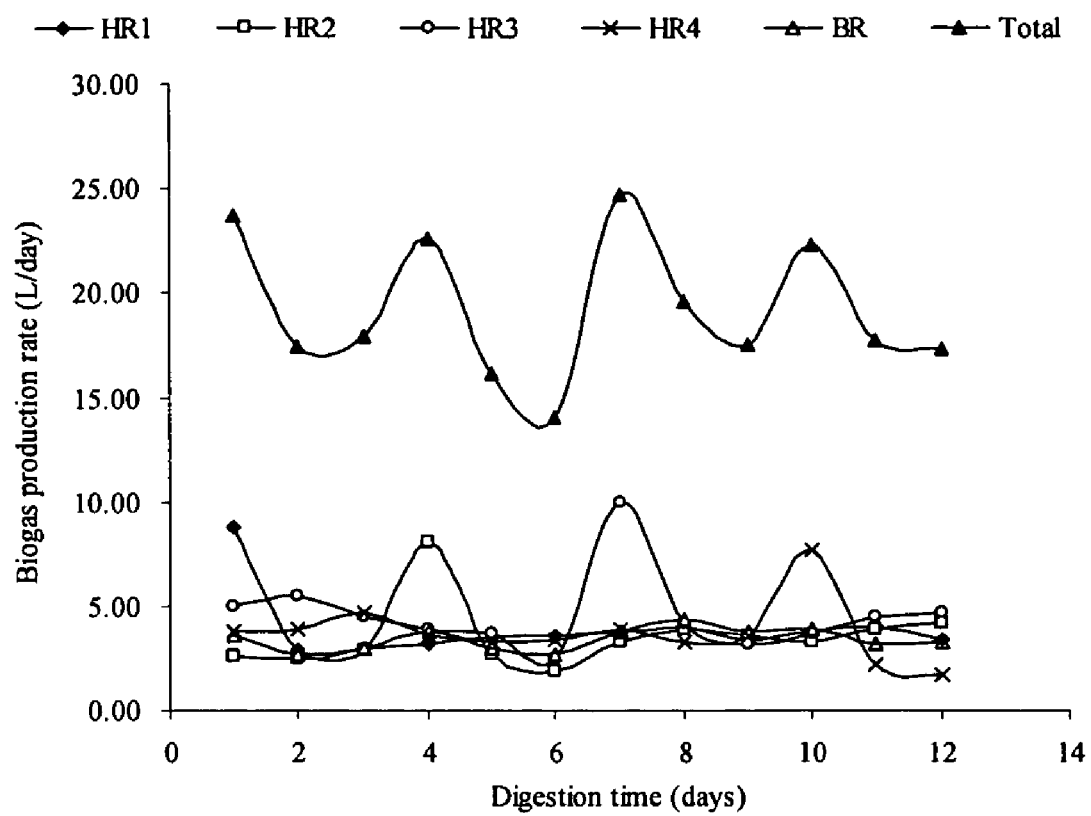
FIG. 9 is a plot of daily biogas production of five reactors in the APS-Digester system during digestion of food waste at a volume ratio of biogasification reactor and hydrolysis reactor of 0.55.
Figure 10:
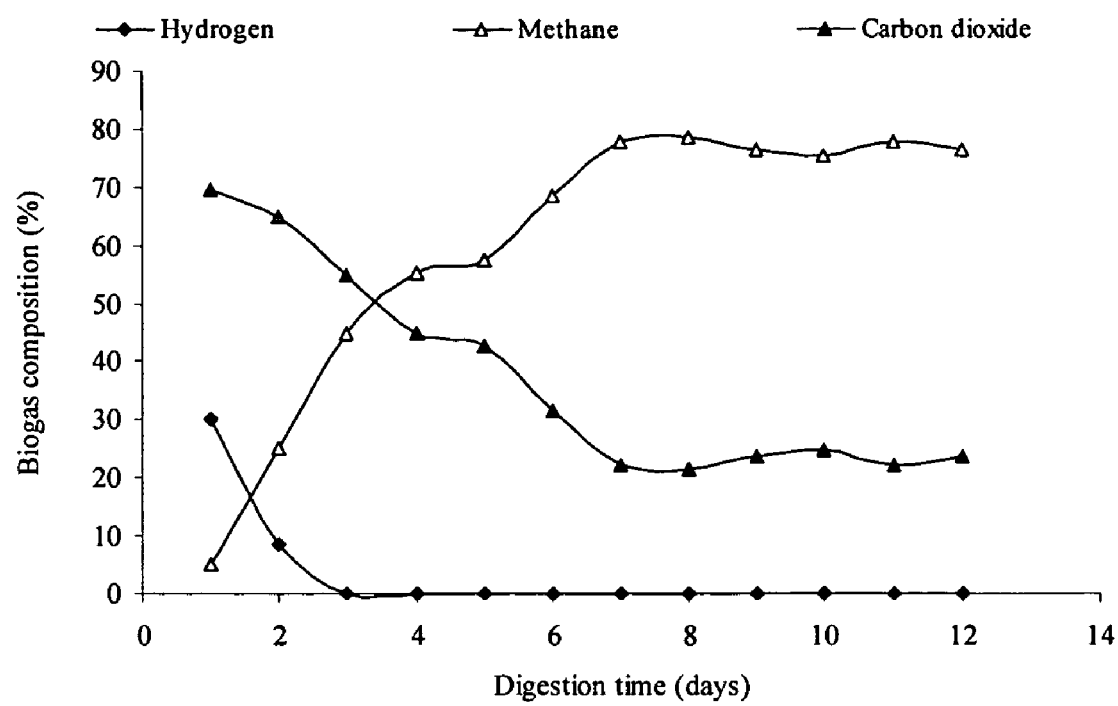
FIG. 10 is a plot of the composition of biogas produced from one of the hydrolysis reactors during digestion of food waste in APS-digester system at a volume ratio of biogasification reactor and hydrolysis reactor BR/HR of 0.55.
Figure 11:
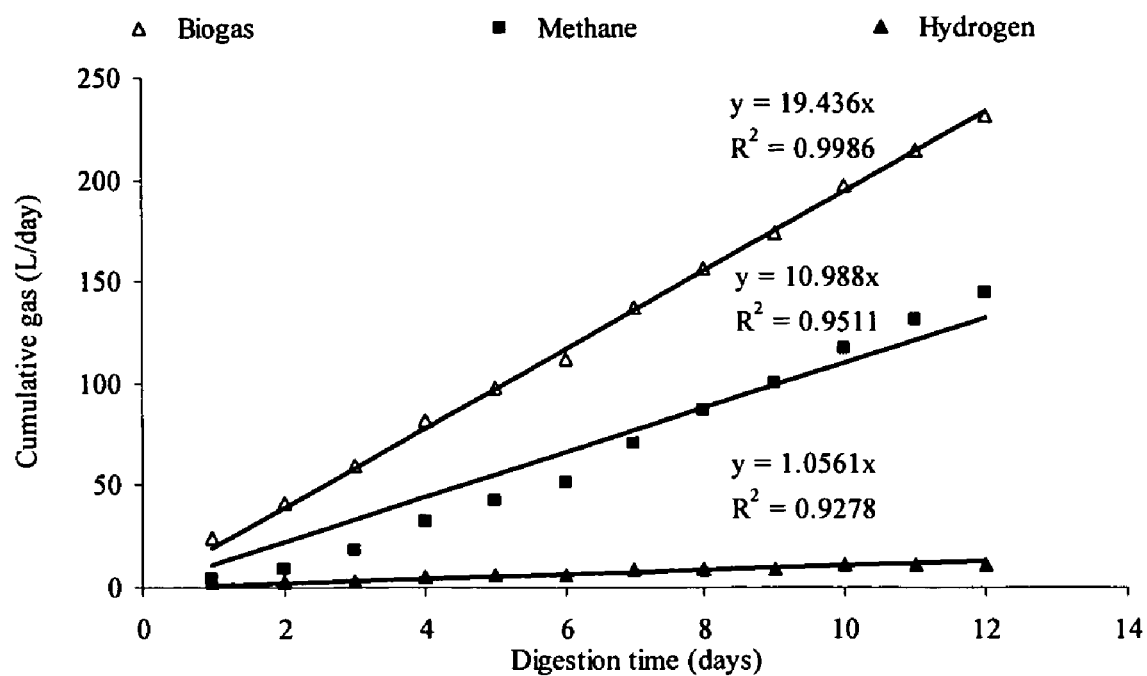
FIG. 11 is a plot of the cumulative production of biogas, methane and hydrogen during digestion of food waste in APS-digester system at a volume ratio of biogasification reactor and hydrolysis reactor of 0.55 ($3^{rd}$ experimental run).

Biogas production rates during the digestion of food wastes using the APS-Digester at BR/HR of 0.55 are shown in FIG. 9. The biogas production rate increased directly after loading a hydrolysis reactor and then declined until loading a next hydrolysis reactor. The total biogas production from the system varied between a maximum of 3.8 L/L/day to a minimum of 3.0 L/L/day with an average biogas production rate of 3.2 L/L/day. A linear increase of both biogas and methane production can be seen. The calculated average biogas and methane yields were 596 and 379 mL/gVS, respectively. The TS and VS reductions in the food waste after 12-day digestion were measured to be 72.4 and 84.5%, respectively (Table 3). These values are higher than those of green waste. The VS reduction values are in line with those reported by Zhang et al. (2007). The measured pH values were 6.7 and 7.8 for hydrolysis and biogasification reactor, respectively.

TABLE 3

Experimental design and performance of the APS-Digester under different conditions

| Run No. | Substrates | BR/HR | Biogas yield (mL/gVS) | Methane yield (mL/gVS) | TS destruction (%) | VS destruction (%) |
|---|---|---|---|---|---|---|
| 1 | Food waste/green waste mixture | 0.93 | 537 | 430 | 72.4 | 74.8 |
| 2 | Food waste/green waste mixture | 0.55 | 461 | 319 | 77.3 | 81.8 |
| 3 | Food waste | 0.55 | 596 | 379 | 72.4 | 84.5 |
| 4 | Green waste | 0.55 | 438 | 252 | 57.8 | 78.0 |
| 5 | Green waste | 0.25 | 438 | 247 | 59.1 | 75.8 | content was almost constant for both BR/HR ratios tested. On average, a methane content of 55% was obtained in the hydrolysis reactors for both systems (data not shown). For both systems, the biogas produced in the biogasification reactor had a higher methane content than the biogas produced from the hydrolysis reactors (data not shown).

Figure 8:
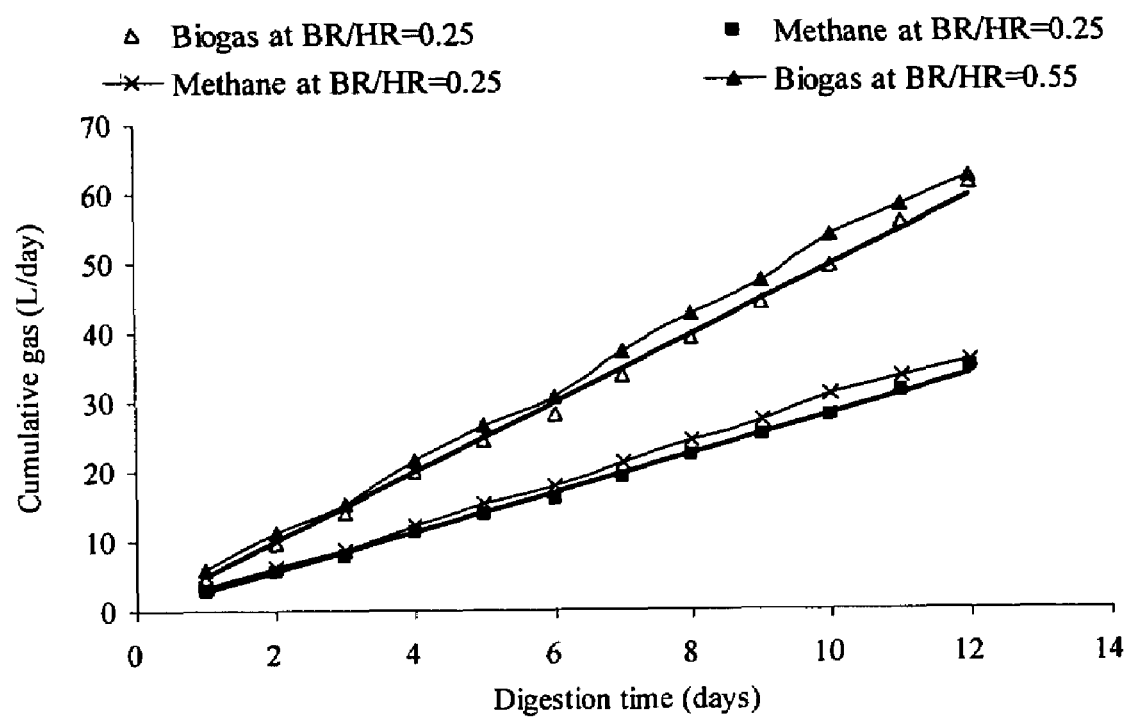
FIG. 8 is a plot of cumulative biogas and methane production in the APS-Digester system during digestion of green waste at volume ratios of biogasification reactor and hydrolysis reactor of 0.55 and 0.25.

The cumulative biogas and methane production from the APS systems are shown in FIG. 8. The biogas and methane

1.9d Conclusions

Application of APS-Digester system for digestion of food waste and green wastes as well as their mixtures was evaluated under thermophilic conditions. BR/HR of 0.55 was used for the digestion of food waste and mixture of food waste and green waste and BR/HR of 0.25 was used for the digestion of green wastes. Under these operation conditions, the average biogas and methane yields were, respectively, 596 and 379 ml/gVS for food waste, 461 and 319 ml/gVS for mixture of food and green wastes, and 438 and 247 ml/gVS for green waste. Hydrogen production was measured when the food waste was digested. It was found that hydrogen yield was 4.9% of the biogas yield. The TS and VS reductions were, respectively, 72.4% and 84.5% for food waste, 77.3% and 81.8% for mixture of food and green wastes, and 59.1% and 75.8% for green waste.

All publications, patents and patent applications mentioned in this specification are herein incorporated by reference into the specification to the same extent as if each individual publication, patent or patent application was specifically and individually indicated to be incorporated herein by reference.

What is claimed is:

1. A method for producing a gas which is a member selected from methane, hydrogen and combinations thereof using two-phase anaerobic digestion of solid organic material, said method comprising:
   (a) incubating a first hydrolysis mixture in a first hydrolysis phase vessel for a first period of incubation, said first hydrolysis mixture comprising said solid organic material and an aqueous liquid, under anaerobic conditions, said first hydrolysis phase vessel comprising therein a hydrolytic bacterial culture for which said solid organic material is a substrate;
   further, incubating a second hydrolysis mixture in a second hydrolysis phase vessel for a fourth period of incubation, said second hydrolysis mixture comprising said solid organic material and an aqueous liquid, under anaerobic conditions, said second hydrolysis phase vessel comprising therein a hydrolytic bacterial culture for which said solid organic material is a substrate;
   (b) after said first period of incubation, transferring a portion of said aqueous liquid of said first mixture residing in said first hydrolysis phase vessel to a buffer tank, forming a buffer tank mixture;
   (c) transferring a portion of said buffer tank mixture to a gasification reactor comprising a methanogenic bacterial culture therein for which said volatile fatty acid is a substrate, forming a biogasification mixture;
   (d) incubating said biogasification mixture for a second incubation period during which gas which is a member selected from methane, hydrogen and mixtures thereof is generated; and
   (e) transferring a portion of said biogasification mixture into said first hydrolysis phase vessel for a third incubation period.

2. The method according to claim 1, wherein step (b) further comprises:
   after said fourth period of incubation, transferring a portion of said aqueous liquid of said second hydrolysis mixture residing in said second hydrolysis phase vessel to said buffer tank mixture, thereby forming a buffer tank mixture which is an equilibrated liquid mixture comprising a volatile fatty acid component from each of said first and second hydrolysis phase vessel.

3. The method according to claim 2, wherein step (e) further comprises:
   transferring a portion of said biogasification mixture into said second hydrolysis phase vessel for a fifth incubation period.

4. The method according to claim 1, wherein said solid organic material is a member selected from the group consisting of sewage sludge, forestry waste, food waste, agricultural waste, green waste, municipal waste and combinations thereof.

5. The method according to claim 1, further comprising collecting said gas generated in said first hydrolysis vessel and said biogasification reactor steps (c) through (e).

6. The method according to claim 1, wherein said gas is generated in step (a).

7. The method according to claim 6, further comprising collecting said gas generated in step (a).

8. The method according to claim 1, wherein said first hydrolysis mixture has a pH of from about 4.5 to about 6.5.

9. The method according to claim 1, wherein said bacterial culture in said first hydrolysis phase vessel is a member selected from the group consisting of *Clostridium, Lactobacillus, Eubacteria* species and combinations thereof.

10. The method according to claim 1, wherein said bacterial culture in said biogasification reactor is a member selected from the group consisting of *Aerobacter, Aeromonas, Alcaligenes, Bacillus, Bacteroides, Clostridium, Eschericia, Klebsiella, Leptospira, Micrococcus, Neisseria, Paracolobacterium, Proteus, Pseudomonas, Rhodopseudomonas, Sarcina, Serratia, Streptococcus and Streptomyces, Methanobacterium omelianskii, Mb. formicium, Mb. sohngenii, Methanosarcina barkerii, Ms. methanica and Mc. Mazei* and mixtures thereof.

11. The method according to claim 1, wherein a member selected from said first hydrolysis vessel, said second hydrolysis vessel, said biogasification reactor and combinations thereof is agitated either continuously or intermittently.

12. The method according to claim 1, wherein said first hydrolysis mixture is transferred from said first hydrolysis phase vessel to said buffer tank through a port on a vertical surface of said first hydrolysis phase vessel.

13. The method according to claim 12, wherein said first hydrolysis phase vessel has an interior that is a single, undivided compartment.

14. The method according to claim 13, wherein from about 80% to about 100% of said first hydrolysis vessel's interior volume contains said first hydrolysis mixture.

15. The method according to claim 1, wherein step (a) further comprises
   incubating multiple hydrolysis mixtures in multiple hydrolysis phase vessels for multiple periods of incubation, said multiple hydrolysis mixtures comprising said solid organic material and an aqueous liquid, under anaerobic conditions, said multiple hydrolysis phase vessels comprising therein a hydrolytic bacterial culture for which said solid organic material is a substrate.

16. The method according to claim 1, wherein said biogasification reactor comprises within it a surface area expanding material which is a medium appropriate for growth of said methanogenic bacterial culture.

17. An anaerobic phased solids digester system for production of gas from solid organic material, said system comprising:
   (a) a first hydrolysis phase vessel comprising therein a bacterial culture for which said solid organic material is a substrate, said hydrolysis vessel further comprising;
      (i) a vessel fluid inlet port communicating fluidically with a first conduit; and
      (ii) a vessel fluid outlet port located on a vertical surface of said hydrolysis phase vessel, said effluent port communicating fluidically with a second conduit;
   (b) a buffer tank comprising;
      (i) a buffer tank outlet port communicating fluidically with a third conduit; and
      (ii) a buffer tank inlet port communicating fluidically with said second conduit;

(c) a biogasification reactor comprising therein a methanogenic bacterial culture, said biogasification reactor further comprising;
 (i) a reactor fluid inlet port communicating fluidically with said third conduit; and
 (ii) and a reactor fluid outlet port communicating fluidically with said first conduit;
(d) a second hydrolysis phase vessel comprising therein a bacterial culture for which said solid organic material is a substrate, said hydrolysis vessel further comprising;
 (i) a vessel fluid inlet port communicating fluidically with a conduit, said conduit communicating fluidically with said reactor fluid outlet port; and
 (ii) a vessel fluid outlet port located on a vertical surface of said hydrolysis phase vessel, said effluent port communicating fluidically with a conduit, said conduit communicating fluidically with said buffer tank inlet port.

18. The digester system according to claim 17, further comprising up to 14 additional hydrolysis phase vessels, each said additional vessel comprising:
 a bacterial culture therein for which said solid organic material is a substrate, each said hydrolysis vessel further comprising;
 (i) a vessel fluid inlet port communicating fluidically with a conduit, said conduit communicating fluidically with said reactor fluid outlet port; and
 (ii) a vessel fluid outlet port located on a vertical surface of said hydrolysis phase vessel, said effluent port communicating fluidically with a conduit said conduit communicating fluidically with said buffer tank inlet port.

19. The digester system according to claim 18, wherein said hydrolysis reactors and said buffer tank are linked in a manner selected from the group consisting of parallel linking, series linking and combinations thereof.

20. The digester system according to claim 19, wherein said hydrolysis reactors are linked in parallel with said methanogenesis reactor.

21. The digester system according to claim 20, wherein said vessel fluid outlet port further comprises a device for interfering with passage of solids into said second conduit.

22. The digester system according to claim 21, wherein said device is a member selected from a grid, filter, grate, sieve, slats, strainer and combinations thereof.

23. The digester system according to claim 17, further comprising a pump operably connected to a member selected from said first hydrolysis reactor, said buffer tank and said biogasification reactor.

* * * * *